United States Patent
Vejarano Restrepo

(10) Patent No.: US 10,507,245 B2
(45) Date of Patent: Dec. 17, 2019

(54) OPHTHALMIC FORMULATION AND METHOD FOR AMELIORATING PRESBYOPIA

(76) Inventor: Luis Felipe Vejarano Restrepo, Popayan (CO)

(*) Notice: Subject to any disclaimer, the term of this patent is extended or adjusted under 35 U.S.C. 154(b) by 939 days.

(21) Appl. No.: 13/553,615

(22) Filed: Jul. 19, 2012

(65) Prior Publication Data
US 2014/0024642 A1 Jan. 23, 2014

(51) Int. Cl.
| | |
|---|---|
| A61K 31/137 | (2006.01) |
| A61K 31/4174 | (2006.01) |
| A61K 31/4178 | (2006.01) |
| A61K 9/00 | (2006.01) |
| A61K 45/06 | (2006.01) |
| A61K 31/167 | (2006.01) |
| A61K 31/4168 | (2006.01) |
| A61K 31/4402 | (2006.01) |

(52) U.S. Cl.
CPC ............ *A61K 45/06* (2013.01); *A61K 31/137* (2013.01); *A61K 31/167* (2013.01); *A61K 31/4168* (2013.01); *A61K 31/4174* (2013.01); *A61K 31/4178* (2013.01); *A61K 31/4402* (2013.01); *A61K 9/0048* (2013.01); *Y10S 514/912* (2013.01)

(58) Field of Classification Search
None
See application file for complete search history.

(56) References Cited

U.S. PATENT DOCUMENTS

| | | | | |
|---|---|---|---|---|
| 4,474,751 | A * | 10/1984 | Haslam et al. | 514/2.4 |
| 4,797,422 | A | 1/1989 | Testa | |
| 4,902,696 | A * | 2/1990 | Conway et al. | 514/320 |
| 5,041,434 | A * | 8/1991 | Lubkin | 514/182 |
| 5,192,780 | A * | 3/1993 | York et al. | 514/357 |
| 5,459,133 | A | 10/1995 | Neufeld | |
| 5,624,962 | A | 4/1997 | Takeuchi et al. | |
| 5,677,321 | A | 10/1997 | Jeon | |
| 5,948,804 | A | 9/1999 | Jeon | |
| 6,040,451 | A | 3/2000 | Jeon | |
| 6,159,998 | A | 12/2000 | Jeon | |
| 6,303,643 | B1 | 10/2001 | Jeon | |
| 6,498,177 | B2 | 12/2002 | Jeon | |
| 6,723,741 | B2 | 4/2004 | Jeon | |
| 7,252,662 | B2 | 8/2007 | Olejniczak Brian L | |
| 8,829,037 | B2 | 9/2014 | Sharma | |
| 2002/0049239 | A1 | 4/2002 | Jeon | |
| 2003/0105147 | A1 | 6/2003 | Jeon | |
| 2004/0137068 | A1 | 7/2004 | Rajiv | |
| 2005/0261641 | A1 | 11/2005 | Tyle | |
| 2006/0100613 | A1 | 5/2006 | Olejniczak | |
| 2006/0166879 | A1 | 7/2006 | Rajiv | |
| 2006/0172972 | A1 | 8/2006 | Rajiv | |
| 2006/0177430 | A1 | 8/2006 | Rajiv | |
| 2007/0299430 | A1 | 12/2007 | Olejniczak | |
| 2009/0156606 | A1 | 6/2009 | Sharma | |
| 2009/0306608 | A1 | 12/2009 | Borgia | |
| 2010/0016395 | A1 | 1/2010 | Benozzi | |
| 2010/0298335 | A1 | 11/2010 | Kaufman | |
| 2011/0104155 | A1 | 5/2011 | Rekik | |
| 2011/0152274 | A1 * | 6/2011 | Kaufman | 514/249 |
| 2011/0160709 | A1 | 6/2011 | Olejniczak | |
| 2011/0281827 | A1 | 11/2011 | Tamarkin | |
| 2011/0301555 | A1 | 12/2011 | Coldren | |
| 2012/0003296 | A1 | 1/2012 | Shantha et al. | |
| 2014/0200211 | A1 * | 7/2014 | Abad | 514/226.5 |

FOREIGN PATENT DOCUMENTS

| | | |
|---|---|---|
| EP | 1938839 B1 | 8/2009 |
| WO | WO 9325199 A1 | 12/1993 |
| WO | WO/9731636 | 9/1997 |
| WO | WO 0064425 A2 * | 11/2000 |
| WO | WO 2004/028420 | 4/2004 |
| WO | WO 2004/058289 | 7/2004 |
| WO | WO 2006/050424 | 5/2006 |
| WO | WO 2008/075149 | 6/2008 |
| WO | WO 2009/112878 | 9/2009 |
| WO | WO 2009/137673 | 11/2009 |
| WO | WO 2010/125416 | 11/2010 |
| WO | WO 2010/135731 | 11/2010 |
| WO | WO 2010125416 A1 | 11/2010 |
| WO | WO 2011/075481 | 6/2011 |
| WO | WO 2011/153284 | 12/2011 |
| WO | WO 2013/041967 | 3/2013 |

OTHER PUBLICATIONS

Takayanagi et al., Difference in mode of action of alpha 1-adrenoceptor antagonists on some vascular smooth muscles and efficacy, Jpn J Pharmacol. Oct. 1986;42(2):237-41, printed from http://www.ncbi.nlm.nih.gov/pubmed/2879058, 1 page, abstract only.*
www.pharmacorama.com, Alpha-1 adrenergic agonists—Vasoconstriction, May 19, 2007, printed from http://web.archive.org/web/20070519021857/http://www.pharmacorama.com/en/Sections/Catecholamines_5_1.php#1, 2 pages.*
www.shriarihant.com, Decongestants—Adrenergic Agonist, Google date stamp of internet entry of Feb. 7, 2009, printed from http://www.shriarihant.com/shriarihantcom/Eye/Decongestants.htm, 3 pages.*
PCT Application No. PCT/US2013/051153, PCT Written Opinion dated Jul. 17, 2014.
MD Eltze "Affinity of the Miotic Drug, Dapiprazole, at alpha-1-Adrenoceptor Subtypes A, B and D" J. Pharm. Pharmacol., vol. 49, No. 30, Mar. 1997, pp. 1091-1095.
PCT Application No. PCT/US2013/051153, PCT International Search Report and Written Opinion dated Sep. 30, 2013 in 12 pages.

(Continued)

*Primary Examiner* — Gigi G Huang
(74) *Attorney, Agent, or Firm* — Knobbe, Martens, Olson & Bear, LLP

(57) ABSTRACT

An ophthalmic formulation having an effective amount of a parasympathomimetic agent comprising pilocarpine, or a pharmaceutically acceptable salt thereof, and one or more α1 adrenergic agonists or antagonists is disclosed. The ophthalmic formulation may enable treatment of conditions adversely affecting the visual acuity of a patient, including presbyopia. A method of using the disclosed ophthalmic formulation to treat or ameliorate symptoms of presbyopia is also disclosed.

10 Claims, No Drawings

(56) References Cited

OTHER PUBLICATIONS

Martin, Xavier D., et al., Vasoconstrictive Effects of Topical Timolol on Human Retinal Arteries, Graefe's Archive for Clinical and Experimental Ophthalmology = Albrecht Von Graefes Archiv Fur Klinische Und Experimentelle Ophthalmologie 1989, vol. 227, No. 6, 1989, pp. 526-530.
Abramson et al., *Pilocarpine in the Presbyope*, Arch Ophthalmol, vol. 89, Feb. 1973 pp. 100-102.
Hanyu et al., "Phenylephrine and Pilocarpine Eye Drop Test for Dementia with Lewy Bodies and Alzheimer's Disease", Neuroscience Letters, vol. 414, No. 2, 2007, p. 174-177.
Mapstone, "Normal Response to Pilocarpine and Phenylephrine," British Journal of Ophthalmology, 1977, 61, pp. 510-511.
Martin X. D. et al.: "Vasoconstrictive Effect of Topical Timolol on Human Retinal Arteries", Graefe's Archive for Clinical and Experimental Ophthalmology = Albrecht vos Graefes Archiv fur Klinsche und Experimentelle Ophthalmologie 1989, vol. 227, No. 6, 1989.
The Merck Index "*An Encyclopedia of Chemicals, Drugs, and Biologicals*". Fourteenth Edition. 2006.—Meloxicam.
Ramsay, "Dilute Solutions of Phenylephrine and Pilocarpine in the Diagnosis of Disordered Autonomic Innervation of the iris: Observations in Normal Subjects, and in the Syndromes of Horner and Holmes-Adie", Journal of the Neurological Sciences, vol. 73, No. 1, Mar. 1986, p. 125-134.
Tabandeh et al., "Phenylephrine and Pilocarpine in the Treatment of Post-Operative Irido-Corneal Adheasion," Eye, vol. 9, 1995, pp. 452-455.

\* cited by examiner

OPHTHALMIC FORMULATION AND METHOD FOR AMELIORATING PRESBYOPIA

BACKGROUND OF THE INVENTION

Field of the Invention

This application relates to a pharmaceutical preparation comprising a parasympathomimetic drug and an α1 (alpha1) adrenergic agonist or antagonist for ameliorating, reducing or treating presbyopia.

Description of the Related Art

Presbyopia is an age-related reduction in visual acuity due to a decline in near focusing ability, commonly associated with blurred appearance of objects at nearby distances. Symptoms of presbyopia often become noticeable by around age 40 to around age 45. Presbyopia is typically associated with the reduced accommodative ability of the eye. For example, flexibility or elasticity of the crystalline lens and strength of the ciliary muscles often decrease with age. A decrease in the flexibility or elasticity of the crystalline lens or the strength of ciliary muscles can be associated with a decrease in the ability of the eye in adjusting the curvature of the crystalline lens to focus on objects at nearby distances, including objects at around a normal reading distance.

Common treatments of presbyopia include use of eye glasses, such as reading glasses typically worn for near distance vision, and bi-focals or multi-focals to provide both improved near and distance vision for patients who already use correction for distance vision. Corrective contact lenses can also be used to treat presbyopia, including bi-focal, multi-focal or monovision contact lenses. Monovision contact lenses typically include a lens for distance vision in one eye, for example a dominant eye, and a lens for near distance vision in the other eye, for example a non-dominant eye. Surgical options are also available for treating presbyopia, including corrective eye surgery. For example, refractive eye surgery generally involves reshaping of the cornea. Refractive surgery can allow reshaping of the cornea in one eye while leaving the other eye untreated, for example correcting vision only in a non-dominant eye for improved near vision while allowing the dominant eye to maintain distance vision. Implantation of intraocular lenses (IOL) can be another surgical option in treating presbyopia, generally involving replacement of the natural lens with a synthetic one. However, eye glasses or corrective lenses may be cumbersome or provide inadequate treatment, while surgical correction can be invasive and are not without risks. Because these techniques merely compensate for the loss of accommodation by changing the way light enters the eye, patients would have to put on the glasses for near vision and remove the glasses for distance vision, or have only one eye corrected for near vision while the other eye remains uncorrected in order to maintain distance vision. Thus, a way to ameliorate or reduce the symptoms of presbyopia while allowing accommodation is needed.

SUMMARY OF THE INVENTION

In some embodiments, an ophthalmic formulation comprises an effective amount of pilocarpine, or a pharmaceutically acceptable salt thereof, and one or more α1 adrenergic agonists or antagonists. The one or more α1 adrenergic agonists or antagonists may be selected from a group consisting of phenylephrine, phenylpropanolamine, etylefrine, oxymetazoline, xilometazoline, tramazoline, and a pharmaceutically acceptable salt thereof.

In some embodiments, a method of ameliorating, reducing or treating presbyopia comprises administering an effective amount of an ophthalmic formulation to an eye of a patient. The ophthalmic formulation may include an effective amount of pilocarpine, or a pharmaceutically acceptable salt thereof, and one or more α1 adrenergic agonists or antagonists. The α1 adrenergic agonist may comprise phenylephrine, or a pharmaceutically acceptable salt thereof.

DETAILED DESCRIPTION OF SOME EMBODIMENTS

The embodiments described in this application relate to a pharmaceutical preparation comprising a parasympathomimetic drug and one or more α1 (alpha1) adrenergic agonists or antagonists. In some embodiment, the pharmaceutical preparation described herein is useful for ameliorating, reducing and/or treating presbyopia or symptoms thereof. The pharmaceutical preparation may reduce or eliminate the symptoms of presbyopia while maintaining the accommodative function of the eyes, and allow patients suffering from presbyopia the ability to focus both far and near. In some embodiments, the pharmaceutical preparation can improve near vision of a patient suffering from presbyopia without affecting the distance vision. In some embodiments, the pharmaceutical preparation may be formulated into an ophthalmic formulation that can be applied to the eye of a patient suffering from conditions relating to presbyopia.

As used herein, the terms ameliorate, treat or treatment refer to a reduction in the severity of symptoms of an eye condition adversely affecting visual acuity. In some embodiments, an ophthalmic formulation as described herein is suitable for treating, or reducing the severity of the symptoms of, presbyopia. For example, an ophthalmic formulation as described herein may be suitable for the treatment of presbyopia by enabling the patient to visually focus on objects at a nearby distance, including objects at around a normal reading distance.

As used herein, the terms effective amount include quantities of one or more active ingredients described herein sufficient for the treatment of a condition of the eye adversely affecting visual acuity, including achieving temporary improvement in the symptoms of presbyopia. For example, effective amounts of an active ingredient when applied to one or both eyes of a patient may enable the patient to visually focus on objects at a nearby distance, including objects at a distance around a normal reading distance.

Some embodiments describe a pharmaceutical preparation comprising an effective amount of a parasympathomimetic drug and one or more α1 adrenergic agonist or antagonist. In some embodiments, the pharmaceutical preparation is an ophthalmic formulation. In some embodiments, the ophthalmic formulation comprising an effective amount of a parasympathomimetic drug and one or more α1 adrenergic agonist or antagonist may further comprise one or more of ingredients selected from the group consisting of a vasoconstricting agent, an anti-histamine agent, a non-steroid anti-inflammatory drug, and an lubricant.

In some embodiments, the parasympathomimetic drug is pilocarpine or a pharmaceutically acceptable salt thereof. Pilocarpine is a direct acting parasympathomimetic agent that acts on $M_3$ muscarinic receptor. It can cause the ciliary muscle in the eye to contract and provide near focus. However, it may also cause contraction of the pupil or miosis.

In some embodiments, the one or more α1 adrenergic agonists or antagonists may independently be selected from phenylephrine, phenylpropanolamine, etylefrine, oxymetazoline, xilometazoline, or tramazoline, or a pharmaceutically acceptable salt thereof. In some embodiments, the α1 adrenergic agonists or antagonists may be phenylephrine. Phenylephrine may dilate the pupil, and may reduce pupil contraction due to pilocarpine. In some embodiments, phenylephrine may contribute to the normal movement of pupil in any light situation, and/or reduces miosis. With proper concentrations of pilocarpine and phenylephrine, voluntary accommodation of the eyes can be maintained or restored while the presbyopia symptoms are ameliorated or treated.

In some embodiments of the ophthalmic formulation, pilocarpine or a pharmaceutically acceptable salt thereof, may be present in the amount of from about 0.1% to about 2.0%, from about 0.1% to about 1.9%, from about 0.2% to about 1.9%, including from about 0.3% to about 1.9%, from about 0.4% to about 1.9%, from about 0.2% to about 1.8%, from about 0.3% to about 1.7%, from about 0.1% to about 1.8%, from about 0.1% to about 1.5%, from about 0.1% to about 1.3%, from about 0.1% to about 1.2% from about 0.1% to about 0.9%, from about 0.1% to about 0.7%, from about 0.4% to about 1.6%, from about 0.5% to about 1.3%, or at about 0.4%, about 0.5%, about 0.6%, about 0.7%, about 0.8%, about 0.9%, about 1.0%, about 1.1%, about 1.2%, by weight.

In some embodiments of the ophthalmic formulation, the phenylephrine or a pharmaceutically acceptable salt thereof, may be present in the amount of from about 0.1% to about 7%, from about 0.1% to about 6%, from about 0.1% to about 5.5%, from about 0.1% to about 4.5%, from about 0.1% to about 3%, from about 0.2% to about 3.5%, from about 0.2% to about 4.5%, from about 0.2% to about 5.5%, from about 0.2% to about 6%, from about 0.3% to about 5%, from about 0.4% to about 4%, from about 0.5% to about 3%, from about 0.6% to about 3%, from about 0.6% to about 2.5%, from about 0.7% to about 2.5%, from about 0.7% to about 2.0%, or about 0.5%, about 1%, about 1.5%, about 2%, about 2.5%, about 3, about 3.5%, about 4%, about 5% by weight.

In some embodiments, an ophthalmic formulation may further comprise a vasoconstricting agent. In some embodiments, a suitable vasoconstricting agent or drug comprises naphazoline, or a pharmaceutically acceptable salt thereof. An ophthalmic formulation suitable for the treating a condition of the eye adversely affecting the visual acuity of a patient, for example presbyopia, may comprise effective amounts of one or more vasoconstricting agents. Alternatively, an ophthalmic formulation may not comprise e a vasoconstricting agent.

For example, an ophthalmic formulation may include by weight from about 0.001% to about 0.020%, including from about 0.002% to about 0.018%, including from about 0.004% to about 0.016%, including from about 0.006% to about 0.01% 2, including from about 0.001% to about 0.015%, including from about 0.001% to about 0.012%, including from about 0.001% to about 0.011%, including from about 0.001% to about 0.010%, including from about 0.001% to about 0.009%, including from about 0.001% to about 0.008%, including from about 0.002% to about 0.008%, including from about 0.003% to about 0.009%, including about 0.002%, about 0.003%, about 0.004%, about 0.005%, about 0.006%, about 0.007%, about 0.008%, about 0.009%, about 0.010%, or about 0.012%, of naphazoline, or a pharmaceutically acceptable salt thereof.

In some embodiments, an ophthalmic formulation also optionally comprises one or more anti-histamine agents. A suitable anti-histamine agent or drug may be independently selected from pheniramine, chlorpheniramine, dexchlorpheniramine, dexbrompheniramine, deschlorpheniramine, triprolidine, brompheniramine, iodopheniramine, fluorpheniramine, or a pharmaceutically acceptable salt thereof. In some embodiments, the anti-histamine agent is pheniramine, or a pharmaceutically acceptable salt thereof. Pheniramine may serve to avoid conjunctival injection or congestion and reduce red eye. It also has a minimal effect on the ciliary muscle, and may improve accommodation. Pheniramine or a pharmaceutically acceptable salt thereof, may be present in an amount of from about 0.01% to about 0.20%, from about 0.05% to about 0.15%, from about 0.02% to about 0.10%, from about 0.03% to about 0.09%, from about 0.04% to about 0.08%, from about 0.02% to about 0.20%, from about 0.04% to about 0.15%, from about 0.04% to about 0.15%, at about 0.01%, about 0.02%, about 0.03%, about 0.04%, about 0.05%, about 0.06%, about 0.07%, about 0.08%, about 0.09%, or about 0.10% by weight in the ophthalmic formulation. Alternatively, an ophthalmic formulation may not comprise an anti-histamine agent.

In some embodiments, an ophthalmic formulation may further comprise a non-steroid anti-inflammatory drugs (NSAID). The NSAID may reduce or eliminate anterior segment inflammation. In some embodiments, a suitable NSAID is independently selected from the group consisting of nepafenac, meloxicam, diclofenac, bendazac, ketorolac, oxyphenbutazone, bromfenac, flurbiprofen, pranoprofen, surprofen, or indomethacin, and a pharmaceutically acceptable salt thereof. In some embodiments, an ophthalmic formulation comprises at least one of nepafenac or meloxicam. Alternatively, an ophthalmic formulation may not comprise a non-steroid anti-inflammatory drug.

In some embodiments, an ophthalmic formulation may be formulated to further comprise an effective amount of a NSAID nepafenac. For example, an ophthalmic formulation formulated to comprise nepafenac may include by weight from about 0.01% to about 0.10%, including from about 0.02% to about 0.09%, including from about 0.03% to about 0.08%, including from about 0.04% to about 0.07%, including from about 0.01% to about 0.09%, including from about 0.01% to about 0.08%, including from about 0.01% to about 0.07%, including from about 0.01% to about 0.06%, including from about 0.01% to about 0.05%, including from about 0.01% to about 0.04%, including from about 0.01% to about 0.03%, including from about 0.02% to about 0.08%, including from about 0.02% to about 0.07%, including from about 0.02% to about 0.06%, including from about 0.02% to about 0.05%, including about 0.02%, about 0.04%, about 0.03%, about 0.04%, or about 0.05% of nepafenac, or a pharmaceutically acceptable salt thereof.

Alternatively, the NSAID may be meloxicam. For example, the ophthalmic formulation may include by weight from about 0.001% to about 0.015%, including from about 0.001% to about 0.014%, including from about 0.001% to about 0.013, including from about 0.001% to about 0.014%, including from about 0.001% to about 0.014%, including from about 0.001% to about 0.012%, including from about 0.01% to about 0.009%, including from about 0.001% to about 0.008%, including from about 0.002% to about 0.007%, including from about 0.002% to about 0.006%, including from about 0.003% to about 0.012%, including from about 0.003% to about 0.01%, including from about 0.003% to about 0.009%, including from about 0.004% to about 0.012%, including about 0.003%, about 0.004%, about 0.005%, about 0.006%, about 0.007%, about 0.008%, about 0.009%, about 0.010%, or about 0.011% of meloxicam, or a pharmaceutically acceptable salt thereof.

An ophthalmic formulation, as described herein, may also further comprise a lubricant or lubricating agent. In some embodiments, the lubricant or lubricating agent may facilitate administration of the ophthalmic formulation. Suitable lubricants can be independently selected from polyethyleneglycol 400 or propyleneglycol. In some embodiments, the ophthalmic formulation comprises one or more suitable lubricants or lubricating agents. Alternatively, an ophthalmic formulation may not comprise a lubricant or lubricating agent.

In some embodiments, where polyethyleneglycol 400 is selected as the lubricant for the ophthalmic formulation, the ophthalmic formulation may comprise by weight of from about 0.01% to about 0.30%, including from about 0.02% to about 0.25%, 0.03% to about 0.20%, 0.04% to about 0.15%, 0.05% to about 0.15%, 0.05% to about 0.10%, 0.10% to about 0.30%, 0.10% to about 0.20%, 0.06% to about 0.20%, 0.05% to about 0.20%, including about 0.05%, about 0.10%, or about 0.15% of polyethyleneglycol 400 or a pharmaceutically acceptable salt thereof.

In some embodiments, the lubricant may be propyleneglycol. For example, an ophthalmic formulation may include by weight of from about 0.01% to about 0.20%, including from about 0.02% to about 0.10%, including from about 0.04% to about 0.09%, including from about 0.04% to about 0.08%, including from about 0.04% to about 0.06%, including from about 0.02% to about 0.10%, including from about 0.02% to about 0.12%, including from about 0.02% to about 0.14%, including from about 0.05% to about 0.20%, including from about 0.05% to about 0.15%, including about 0.01%, about 0.02%, about 0.03%, about 0.04%, about 0.05%, about 0.06%, about 0.07%, about 0.08%, about 0.09%, or about 0.10% of propyleneglycol or a pharmaceutically acceptable salt thereof.

In some embodiments, the ophthalmic formulation comprises one or more components to facilitate application of the ophthalmic formulation. For example, the ophthalmic formulation may also optionally comprise a pharmaceutically acceptable carrier, antibacterial agent, or a preservative. In some embodiments, a pharmaceutically acceptable carrier comprises purified water.

Some embodiments described herein relate to a method of treating a condition of the eye adversely affecting near distance visual acuity of a patient, including ameliorating symptoms of presbyopia. A method of treating the symptoms of presbyopia may include applying to one or both eyes of a patient an ophthalmic formulation as described herein. The ophthalmic formulation may be applied to the eye of a patient as a liquid, a gel, a solution, a suspension, or any combination thereof. In some embodiments, the ophthalmic formulation is administered to the eye via an ocular route, including topical application to the conjunctiva.

An ophthalmic formulation may comprise one or more components, each component may be administered sequentially or simultaneously to the one or both eyes of a patient for improved visual acuity, including for the treatment of the symptoms of presbyopia. For example, application of an ophthalmic formulation comprising an effective amount of a parasympathomimetic agent and an effective amount of an α1 adrenergic agonist or antagonist may ameliorate symptoms of presbyopia while allowing voluntary accommodation.

In some embodiments, an ophthalmic formulation as described herein is applied to one or both eyes of a patient showing symptoms of presbyopia to improve the ability of the patient to focus on objects at a nearby distance, including objects at around a normal reading distance. In some embodiments, application of an ophthalmic formulation as described herein may sufficiently improve the near distance visual acuity of a patient independent of other methods of treatment. For example, administration of an ophthalmic formulation as described herein may enable a patient to focus on objects at a distance around a normal reading distance without use of corrective lenses or corrective eye surgery. Administration of the ophthalmic formulation may relieve symptoms for a patient in the early stages of presbyopia, including enabling near distance visual acuity without use of corrective lenses or glasses.

In some embodiments, an ophthalmic formulation as described herein is administered to a patient having symptoms of presbyopia, in addition to symptoms from myopia or hyperopia to facilitate near distance visual acuity such that the patient may not need to depend on the corrective treatment such as bifocals/multi-focals lenses or monovision contact lenses or to remove the glasses to read in myopes.

In some embodiments, an ophthalmic formulation as described herein is administered to one or both eyes of a patient to provide treatment for presbyopia as an alternative to corrective eye surgery. For example, an ophthalmic formulation as described herein may be administered to a patient having symptoms of presbyopia where the patient either prefers not to or cannot receive corrective eye surgery to treat presbyopia. The ophthalmic formulation as described herein may also be administered to a myopic or hyperopic patient (with or without astigmatism) having symptoms of presbyopia, but prefers to receive treatment only for the far vision defect. Alternatively, an ophthalmic formulation as described herein may be administered to a patient who continues to have symptoms of presbyopia after the patient has undergone corrective eye surgery for presbyopia. The ophthalmic formulation may be used in conjunction with corrective eye surgery for presbyopia to further reduce the symptoms of presbyopia. In some embodiments, the ophthalmic formulation as described herein is applied to one or both eyes of a patient to reduce a decline in near distance visual acuity after undergoing a corrective eye surgery for far vision at a younger age.

In some embodiments, administration of an ophthalmic formulation as described herein facilitates improvement in the symptoms of presbyopia for a patient who has reversed a previously received corrective eye surgery for presbyopia. For example, administration of the ophthalmic formulation may enable reestablishment of binocularity for a patient after a reversal or regression of a previously received monovision laser surgery for treating presbyopia.

In some embodiments, an ophthalmic formulation as described herein is administered to a patient to improve the ability of the patient to focus on nearby objects after the patient has undergone corrective surgery for treatment of ocular conditions other than presbyopia, including for example a corrective eye surgery for the treatment of a cataract.

In some embodiments, an ophthalmic formulation as described herein is used in conjunction with other treatments for eye conditions, including treatments for the symptoms of presbyopia. For example, an ophthalmic formulation as described herein may be administered to a patient in conjunction with use of mono-focal intraocular lenses, multi-focal intraocular lenses, or accommodative intraocular lenses to improve the near focusing ability of the patient.

In some embodiments, application of an ophthalmic formulation as described herein is suitable for reducing the symptoms of ocular hypertension. The ophthalmic formulation may be administered to an eye of a patient to improve symptoms of ocular hypertension through a reduction in intraocular pressure.

Although this invention has been disclosed in the context of certain embodiments and examples, it will be understood by those skilled in the art that the invention extends beyond the specifically disclosed embodiments to other alternative embodiments and/or uses of the invention and obvious modifications and equivalents thereof. In addition, while several variations of the embodiments of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the embodiments of the disclosed invention. Thus, it is intended that the scope of the invention herein disclosed should not be limited by the particular embodiments described above.

What is claimed is:

1. An ophthalmic formulation comprising an effective amount of about 0.26% pilocarpine or a pharmaceutically acceptable salt thereof, about 0.5% phenylephrine or a pharmaceutically acceptable salt thereof, and about 0.003% naphazoline or a pharmaceutically acceptable salt thereof.

2. The ophthalmic formulation of claim 1, further comprises an anti-histamine selected from the group consisting of pheniramine, chlorpheniramine, dexchlorpheniramine, dexbrompheniramine, deschlorpheniramine, triprolidine, brompheniramine, iodopheniramine, fluorpheniramine, and a pharmaceutically acceptable salt thereof.

3. The ophthalmic formulation of claim 2, wherein the anti-histamine is pheniramine or a pharmaceutically acceptable salt thereof.

4. The ophthalmic formulation of claim 3, wherein the pheniramine is present in an amount of about 0.03% to about 0.09% by weight.

5. The ophthalmic formulation of claim 1, further comprises an non-steroidal anti-inflammatory drug.

6. The ophthalmic formulation of claim 5, wherein the non-steroidal anti-inflammatory drug is selected from the group consisting of nepafenac, meloxicam, diclofenac, bendazac, ketorolac, oxyphenbutazone, bromfenac, flurbiprofen, pranoprofen, surprofen, indomethacin, and a pharmaceutically acceptable salt thereof.

7. The ophthalmic formulation of claim 5, wherein the non-steroidal anti-inflammatory drug is selected from the group consisting of nepafenac, bromfenac, and meloxicam.

8. A method of ameliorating, reducing or treating presbyopia comprising administering an effective amount of an ophthalmic formulation of claim 1 to an eye of a patient.

9. The method of claim 8, wherein the ophthalmic formulation further comprises an anti-histamine selected from the group consisting of pheniramine, chlorpheniramine, dexchlorpheniramine, dexbrompheniramine, deschlorpheniramine, triprolidine, brompheniramine, iodopheniramine, fluorpheniramine, and a pharmaceutically acceptable salt thereof.

10. The method of claim 9, wherein the ophthalmic formulation further comprises a non-steroidal anti-inflammatory drug selected from the group consisting of nepafenac, meloxicam, diclofenac, bendazac, ketorolac, oxyphenbutazone, bromfenac, flurbiprofen, pranoprofen, surprofen, indomethacin, and a pharmaceutically acceptable salt thereof.

* * * * *

UNITED STATES PATENT AND TRADEMARK OFFICE
CERTIFICATE OF CORRECTION

PATENT NO. : 10,507,245 B2
APPLICATION NO. : 13/553615
DATED : December 17, 2019
INVENTOR(S) : Luis Felipe Vejarano Restrepo It is certified that error appears in the above-identified patent and that said Letters Patent is hereby corrected as shown below:

On the Title Page

Page 2, Column 1, item (56), Other Publications, Line 15, delete "vos" and insert --Von--.

Page 2, Column 1, item (56), Other Publications, Line 15, delete "Klinsche" and insert --Klinische--.

Page 2, Column 1, item (56), Other Publications, Line 25, delete "Adheasion,"" and insert --Adhesion,"--.

In the Specification

Column 1, Lines 65-66, delete "etylefrine," and insert --etilefrine,--.

Column 1, Line 66, delete "xilometazoline," and insert --xylometazoline,--.

Column 3, Line 3, delete "etylefrine," and insert --etilefrine,--.

Column 3, Line 4, delete "xilometazoline," and insert --xylometazoline,--.

Column 4, Line 3, delete "deschlorpheniramine," and insert --dexchlorpheniramine,--.

Column 4, Lines 4-5, delete "fluorpheniramine," and insert --fluoropheniramine,--.

Column 4, Line 30, delete "surprofen," and insert --suprofen,--.

In the Claims

Column 7, Line 34, Claim 2, delete "deschlorpheniramine," and insert --dexchlorpheniramine,--.

Column 7, Line 35, Claim 2, delete "fluorpheniramine," and insert --fluoropheniramine,--.

Signed and Sealed this
Seventh Day of April, 2020

Andrei Iancu
*Director of the United States Patent and Trademark Office*

CERTIFICATE OF CORRECTION (continued)
U.S. Pat. No. 10,507,245 B2

Column 8, Line 14 (approx.), Claim 6, delete "surprofen," and insert --suprofen,--.

Column 8, Lines 25-26 (approx.), Claim 9, delete "deschlorpheniramine," and insert --dexchlorpheniramine,--.

Column 8, Line 27 (approx.), Claim 9, delete "fluorpheniramine," and insert --fluoropheniramine,--.

Column 8, Line 34 (approx.), Claim 10, delete "surprofen," and insert --suprofen,--.